United States Patent [19]

Imada

[11] Patent Number: 4,576,760

[45] Date of Patent: Mar. 18, 1986

[54] HYDROQUINONE SULFATE DERIVATIVES AND PRODUCTION THEREOF

[75] Inventor: Isuke Imada, Izumi, Japan

[73] Assignee: Takeda Chemical Industries, Ltd., Osaka, Japan

[21] Appl. No.: 604,495

[22] Filed: Apr. 27, 1984

[30] Foreign Application Priority Data

May 2, 1983 [JP] Japan .................................. 58-77819

[51] Int. Cl.$^4$ ........................................... C07C 141/16
[52] U.S. Cl. ........................................ 558/37; 558/24
[58] Field of Search ......................................... 260/457

[56] References Cited

U.S. PATENT DOCUMENTS

| | | | |
|---|---|---|---|
| 3,728,363 | 4/1973 | Morimoto et al. | 260/396 R |
| 3,849,453 | 11/1974 | Morimoto et al. | 260/396 R |
| 4,139,545 | 2/1979 | Morimoto et al. | 260/396 R |
| 4,358,461 | 11/1982 | Maki et al. | 424/331 |
| 4,436,753 | 3/1984 | Imada et al. | 424/331 |

OTHER PUBLICATIONS

Watanabe et al., Biochemistry, vol. 9, No. 14, 2879-2886 (1970).

*Primary Examiner*—Nicky Chan
*Attorney, Agent, or Firm*—Wenderoth, Lind & Ponack

[57] ABSTRACT

A compound of the formula:

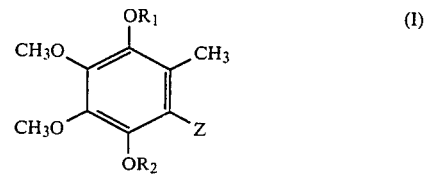

[wherein either one of $R_1$ and $R_2$ stands for hydrogen or $SO_3H$ and the other is $SO_3H$, Z stands for

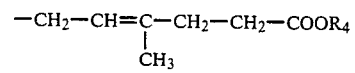

$$-CH_2-CH=C-CH_2-CH_2-COOR_4$$
$$\phantom{-CH_2-CH=}|$$
$$\phantom{-CH_2-CH=}CH_3$$

(where m denotes an integer of 1-22, n denotes an integer of 0-21, $R_3$ stands for hydrogen or an acyl group having 2 to 4 carbon atoms, and $R_4$ is hydrogen or an alkyl group having 1 to 4 carbon atoms)] and pharmacologically acceptable salts thereof, which has various pharmacological actions such as antioxidative action, inhibitory action of SRS-A generation, immunoregulatory action, action on lysosome-membrane, cell-activating action, phosphodiesterase-inhibitory action, etc.

8 Claims, No Drawings

HYDROQUINONE SULFATE DERIVATIVES AND PRODUCTION THEREOF

This invention relates to medicinally useful novel hydroquinone derivatives having various pharmacological actions such as antioxidative action in living bodies, and a method of preparing them.

For the therapy of, for example, vascular disturbances in cerebral, cardiac or other organs, an antioxidant for inhibiting peroxidation of lipid is used in general. The present inventor's search for compounds having excellent antioxidative action has led to the finding of novel compounds meeting this purpose.

The present invention relates to, more concretely:
1. A compound of the formula:

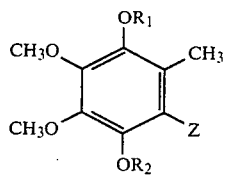

[wherein either one of $R_1$ and $R_2$ stands for hydrogen or $SO_3H$ and the other one is $SO_3H$, Z stands for

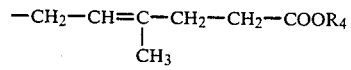

(where m denotes an integer of 1–22, n denotes an integer of 0–21, $R_3$ stands for hydrogen or an acyl group having 2 to 4 carbon atoms, and $R_4$ is hydrogen or an alkyl group having 1 to 4 carbon atoms)] and pharmacologically acceptable salts thereof [hereinafter referred to as Compound (I)];

2. A method of preparing Compound (I), which comprises reacting a compound of the formula:

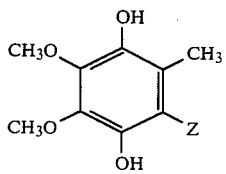

[wherein Z is as defined above] with a sulfating agent; and

3. A method of preparing Compound (I) which comprises reacting a compound of the formula:

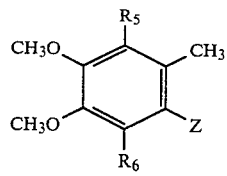

[wherein either one of $R_5$ and $R_6$ stands for hydrogen and the other is hydroxyl and Z has the meaning given above] or a salt thereof [hereinafter referred to as Compound (III)] with a salt of peroxodisulfuric acid in the presence of a base.

As the acyl groups having 2 to 4 carbon atoms represented by $R_3$ of the group $-(CH_2)_m-OR_3$ represented by Z in the aforementioned general formulae (I), (II) and (III), there may be mentioned acetyl, propionyl or butylyl. The alkyl groups having 1 to 4 carbon atoms represented by $R_4$ of the groups

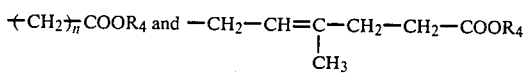

may be exemplified by methyl, ethyl, propyl and butyl.

As the pharmacologically acceptable salts of the compounds of the formula (I), there may be mentioned, for example, aluminium salts, zinc salts, ammonium salts and salts with organic amines (e.g. triethylamine, pyridine) as well as alkali metal salts such as sodium salts and potassium salts.

The method of the reaction of a compound of the formula (II) with a sulfating agent is usually conducted by allowing a compound of the formula (II) to contact a sulfating agent in a solvent. As the sulfating agent employed for this reaction, there may be mentioned, for example, (1) sulfuric acid and (2) a complex of sulfur trioxide and a weak base. As the weak base, there may be mentioned, among others, a primary amine such as methylamine or ethylamine, a secondary amine such as dimethyl amine or diethyl amine, and a tertiary amine such as trimethyl amine, triethyl amine or pyridine. The complex of sulfur trioxide with a weak base can be prepared by allowing halogenosulfonic acid (e.g. chlorosulfonic acid) to react with a weak base (e.g. amines). As the solvent, there may be mentioned a basic solvent such as pyridine or dimethylaniline, a halogenated hydrocarbon such as chloroform, carbon tetrachloride, 1,1-dichloroethane or 1,2-dichloroethane, and carbon disulfite. The molar ratio of the compound of the formula (II) relative to the sulfating agent is, when preparation of a monosulfuric ester is intended, 1:1–2, preferably 1:1–1.2, and, when a di-sulfuric ester is desired, 1:1.5–4, preferably 1:2–3. The reaction temperature ranges from $-15°$ C. to the boiling point of the solvent, preferably from $0°$ C. to room temperature, and the reaction time is usually about 3–48 hours. In the method of this invention, the compound of the formula (II), halogenosulfonic acid and a weak base can be subjected to reaction altogether. In this case, it appears that halogenosulfonic acid reacts first with the weak base to produce a complex of sulfur trioxide and the weak base, which then reacts with the compound of the formula (II) to yield Compound (I).

The method of the reaction of Compound (III) with a salt of peroxodisulfuric acid is usually conducted by allowing Compound (III) to contact a salt of peroxodisulfate in a solvent in the presence of a base. In this reaction, the peroxodisulfate is shown by the general formula $M_2S_2O_8$, [wherein M stands for an alkali metal atom or ammonium]. As the alkali metal atom represented by M in the formula, there may be mentioned, for example, sodium or potassium. As the salt of a compound of the formula (III), there may be exemplified sodium salt or potassium salt. As the solvent are exemplified water or pyridine, and as the base are exemplified sodium hydroxide, potassium hydroxide or pyridine. When pyridine is used as the base, it takes a role of the solvent as well. The amount of the base is 1–10 moles relative to 1 mole of Compound (III), preferably 3–8 moles. The molar ratio of Compound (III) to a salt of peroxodisulfate is 1:1–3, preferably 1:1–1.2. The reaction temperature ranges usually from 0° C. to room temperature, but, preferably, not higher than 20° C. The reaction time is usually 12–24 hours. By this reaction, Compound (I) can be obtained in the form of an alkali salt.

Compound (I) thus obtained, when it is in the form of a salt, can be converted, upon necessity, to a free acid by the addition of an acid. And, when it is in the form of a free acid, it can be converted, upon necessity, to a salt by the addition of an alkali.

Compound (I) can be isolated and purified by per se known means, for example, concentration, concentration under reduced pressure, crystallization, recrystallization, chromatography or extraction.

Pharmacological actions of Compound (I) of this invention are as follows:

1. Inhibition Rate of Peroxidation of Lipids

In accordance with the method of Kornbrust and Mavis [Mol. Pharm., 17, 400 (1980)], inhibition rate of peroxidation of lipids was determined. The results are as shown in Table 1.

TABLE 1

| Compound | Concentration | Inhibition Rate of Peroxidation of Lipids* |
| --- | --- | --- |
| potassium salt of 6-(10-hydroxydecyl)-2,3-dimethoxy-5-methylhydroquinone 1-sulfate | $1 \times 10^{-5}$ M | 28% |
| | $1 \times 10^{-4}$ M | 59% |

Note*: Homogenized livers of rats were incubated in the presence of NADPH/Fe$^{++}$. The amounts of malondialdehyde formed due to the peroxidation of lipids were compared.

2. Action of Inhibiting cAMP phosphodiesterase

In accordance with the method of Butcher and Sutherland [J. Biol. Chem., 237, 1244 (1962)], the action of inhibiting cAMP phosphodiesterase was determined. The results are as shown in Table 2.

TABLE 2

| Compound | Concentration | Inhibition rate of phosphodiesterase** |
| --- | --- | --- |
| potassium salt of 6-(10-hydroxydecyl)-2,3-dimethoxy-5-methyl-hydroquinone 1-sulfate | $5 \times 10^{-4}$ M | 70% |
| | $1 \times 10^{-3}$ M | 89% |

**Amounts of inorganic phosphoric acid produced by decomposition of cyclic AMP with phosphodiesterase from beef heart and 5'-nucleotidase.

Compounds (I) of this invention have, among others, anti-oxidative action, inhibitory action on SRS-A generation, immunoregulatory action, action on lysosome-membrane, cell-activating action and phosphodiesterase-inhibitory action. On the other hand, the toxicity of Compounds (I) is relatively low in general. For example, their LD$_{50}$ in mice by intravenous injection is 500–1000 mg/kg.

In animals, especially mammals (e.g. rays, mice, guinea pigs, dogs, rabbits, humans, etc.), Compounds (I) show hypotensive, analgesic, anti-ulcer, antiinflammatory, diuretic immunoregulatory, antiasthmatic, antiallergic, blood-platelet-aggregation inhibitory and cerebral circulation improving actions, and can be used as pharmaceuticals such as a blood pressure lowering, analgesic, anti-ulcer, anti-inflammatory, diuretic, immuno-regulating, anti-asthmatic, anti-allergic, anti-coagulant, or cerebral-circulation-improving agent. Thus, they are useful for the therapy or prophylaxis of, for example, hypertension, cerebral thrombosis, ischemic heart diseases, coronary insufficiency, diseases associated with disturbance of prostaglandin- and thromboxan-biosynthesis, immuno-deficiency, bronchial asthma or allergy.

Compound (I) of this invention can be safely administered orally or parenterally as it is or as an active ingredient of medicine [e.g. tablets, capsules (including soft capsules and microcapsules), solutions, injections, supositories] mixed with pharmacologically acceptable carriers or excipients (e.g. lactose, starch, sugar, magnesium stearate, etc.). The doses depend on the subjects, administration route or symptoms of the patients, but, in case of oral administration to adult patients with hypertension or bronchial asthma, the dose is about 0.04–25 mg/kg, preferably about 0.1–10 mg/kg, more preferably 0.5 to 5 mg/kg body weight at one time, 1–3 times a day.

Among Compounds (I), those wherein either one of $R_1$ and $R_2$ is hydrogen are superior in pharmaceutical effect to those wherein both $R_1$ and $R_2$ are SO$_3$H.

The present invention will be explained more concretely by the following reference examples and working examples, but they should be understood as not limiting the scope of this invention.

EXAMPLE 1

To a solution of 6-(5-carboxy-3-methyl-2-pentenyl)-2,3-dimethoxy-5-methyl-1,4-benzoquinone (93 mg) in methanol (3 ml) was added p-toluene sulfonic acid (10 mg). The mixture was stirred for 4 hours. The solvent was evaporated off under reduced pressure. The residue was dissolved in diethylether. The solution was washed with water and then dried. The solvent was evaporated off under reduced pressure. The residue was subjected to a column chromatography using silica-gel (3 g). From the fractions eluted with carbon tetrachloride-ethyl acetate (5:1) was obtained 2,3-dimethoxy-6-(5-methoxycarbonyl-3-methyl-2-pentenyl)-5-methyl-1,4-benzoquinone (84 mg). This product was treated in a conventional manner to produce 2,3-dimethoxy-6-(5-methoxycarbonyl-3-methyl-2-pentenyl)-5-methylhydroquinone, which was dissolved in pyridine (0.4 ml). The solution was cooled to about −10° C., to which was added chlorosulfonic acid (120 μl). The mixture was stirred for two days at room temperature. The reaction solution was made to pH 8–9 with 1N potassium carbonate, then unreacted substances were removed by extraction with diethylether. The aqueous phase was subjected to evaporation to dryness under reduced pressure. The residue was subjected to column-chromatography using silica-gel (3 g). From the fractions eluted with methanol-chloroform (2:5) was obtained a mixture (24 mg) of potassium salts of 2,3-dimethoxy-6-(5-methoxycarbonyl)-3-methyl-2-pentenyl)-5-methylhydroquinone 1-sulfate and 4-sulfate.

NMR (D$_2$O) δ: 1.62 (3H, s, =CCH$_3$), 1.94 and 2.04 (3H, s, CH$_3$ on the ring), 2.10–2.49 (4H, m, CH$_2$COO, =CCH$_2$), 3.05–3.29 (2H, m, CH$_2$ on the ring), 3.35 (3H, s, COOCH$_3$), 3.70 (3H, s, OCH$_3$), 3.79 (3H, s, OCH$_3$)

From the fractions eluted with methanol was obtained dipotassium salt of 2,3-dimethoxy-6-(5-methoxycarbonyl-3-methyl-2-pentenyl)-5-methylhydroquinone 1,4-disulfate.

NMR (D$_2$O) δ: 1.67 (3H, s, =CCH$_3$), 2.10 (3H, s, CH$_3$ on the ring), 2.17–2.57 (4H, m, CH$_2$COO, =CCH$_2$), 3.24 (2H, m, CH$_2$ on the ring), 3.37 (3H, s, COOCH$_3$), 3.79 (6H, s, OCH$_3$)

EXAMPLE 2

By a conventional manner, 6-(3-carboxypropyl)-2,3-dimethoxy-5-methyl-1,4-benzoquinone was converted to 6-(3-carboxypropyl)-2,3-dimethoxy-5-methylhydroquinone, and a pyridine solution of the compound was added to a solution of a complex of sulfur trioxide.-triethylamine in pyridine while stirring under cooling (dry ice-acetone). Excess solvent was removed by evaporation under reduced pressure. The residue was dissolved in methanol which was left standing to produce the methylester. To this solution was added sodium hydroxide to made its pH 8, which was then subjected to purification by means of DEAE cellulose column. From the first column was obtained a mixture (24 mg) of sodium salts of 2,3-dimethoxy-6-(3-methoxycarbonylpropyl)-5-methylhydroquinone 1-sulfate and 4-sulfate.

IR spectrum: $\nu_{max}^{KBr}$ cm$^{-1}$: 1730 (COOCH$_3$), 1250 (S=O), 1050 (C—O—S)

NMR (D$_2$O) δ: 1.66–1.94 (2H, m, CH$_2$), 2.14 & 2.23 (3H, s, CH$_3$ on the ring), 2.42 (2H, t, J=7 Hz, CH$_2$COO), 2.64 & 2.80 (2H, t, J=7 Hz, CH$_2$ on the ring), 3.66 (3H, s, COOCH$_3$), 3.86 (3H, s, OCH$_3$), 3.93 (3H, s, OCH$_3$)

UV spectrum: $\lambda_{max}^{EtOH}$ nm: 276, 282.5

White powdery product obtained from the second fraction was recrystallized from a small volume of water to give sodium salt of 2,3-dimethoxy-6-(3-methoxycarbonylpropyl)-5-methylhydroquinone 4-sulfate as colorless crystals, m.p. 82°–85° C.

NMR (D$_2$O) δ: 1.65–1.93 (2H, m, CH$_2$), 2.23 (3H, s, CH$_3$ on the ring), 2.42 (2H, t, J=7 H, CH$_2$COO), 2.66 (2H, t, J=7 Hz, CH$_2$ on the ring), 3.65 (3H, s, COOCH$_3$), 3.86 (3H, s, OCH$_3$), 3.92 (3H, s, OCH$_3$)

Elemental Analysis for C$_{14}$H$_{19}$NaO$_9$S.3H$_2$O: Calcd.: C,38.18; H,5.72; S,7.27; Found: C,37.98; H,5.85; S,7.08

UV spectrum $\lambda_{max}^{EtOH}$ nm(ε): 275 (1334), 282.5 (1532)

EXAMPLE 3

Employing 6-(10-acetoxdecyl)-2,3-dimethoxy-5-methylhydroquinone (1.27 g) as the starting material, chlorosulfonic acid in pyridine was allowed to react therewith as in the manner of Example 1. The reaction mixture was made to pH 8–9 with 1N sodium hydroxide, and then worked up as in Example 1.

From the first fraction of a silica-gel chromatography, was obtained a mixture (698 mg) of sodium salts of 6-(10-acetoxydecyl)-2,3-dimethoxy-5-methylhydroquinone 1-sulfate and 4-sulfate.

IR spectrum $\nu_{max}^{KBr}$ cm$^{-1}$: 1730 (OCOCH$_3$), 1250 (S=O), 1050 (C—O—S)

NMR (D$_2$O) δ: 1.23 (16H, b, CH$_2$), 1.99 (3H, s, OCOCH$_3$), 2.08 & 2.21 (3H, s, CH$_3$ on the ring), 2.44–2.80 (2H, m, CH$_2$ on the ring), 3.80 (3H, s, OCH$_3$), 3.88 (3H, s, OCH$_3$), 3.98 (2H, t, CH$_2$O)

From the second fraction was obtained disodium salt (153 mg) of 6-(10-acetoxydecyl)-2,3-dimethoxy-5-methylhydroquinone 1,4-disulfate.

IR spectrum $\nu_{max}^{KBr}$ cm$^{-1}$: 1740 (OCOCH$_3$), 1250 (S=O), 1050 (C—M—S)

NMR (D$_2$O) δ: 1.17 (16H, b, CH$_2$), 1.99 (3H, s, OCOCH$_3$), 2.19 (3H, s, CH$_3$ on the ring), 2.71 (2H, t, CH$_2$ on the ring), 3.86 (6H, s, OCH$_3$), 3.99 (2H, t, J=6 Hz, CH$_2$O)

Elemental Analysis for C$_{21}$H$_{32}$Na$_2$O$_{12}$S$_2$.4H$_2$O: Calcd.: C,38.73; H,6.15; S,9.84; Found: C,38.53; H,5.72; S,9.31

EXAMPLE 4

6-(10-Acetoxydecyl)-2,3-dimethoxy-5-methylhydroquinone (3.8 g) was converted to its sulfuric acid ester, whose pH was made to around 8–9 with 1N KOH, followed by working up as in the manner of Example 1 to give a mixture (1.1 g) of potassium salts of 6-(10-acetoxy-decyl)-2,3-dimethoxy-5-methylhydroquinone 1-sulfate and 4-sulfate.

NMR (D$_2$O) δ: 1.18 (116H, b, CH$_2$), 1.90 (3H, s, OCOCH$_3$), 1.98 & 2.11 (3H, s, CH$_3$ on the ring), 2.46 (2H, m, CH$_2$ on the ring), 3.70 (3H, s, OCH$_3$), 3.80 (3H, s, OCH$_3$)

EXAMPLE 5

The mixture (24 mg) of potassium salts of 2,3-dimethoxy-6-(5-methoxycarbonyl-3-methyl-2-pentenyl)-5-methylhydroquinone 1-sulfate and 4-sulfate obtained in Example 1 was dissolved in 1N KOH (0.5 ml). The solution was heated at 60° C. for two hours. The reaction solution was subjected to a Sephadex LH-20 column chromatography. Elution was conducted with water. The object fraction was subjected to evaporation to dryness under reduced pressure, followed by treating with methanol-ethylether to give a mixture (12 mg) of dipotassium salts of 6-(5-carboxy-3-methyl-2-pentenyl)-2,3-dimethoxy-5-methylhydroquinone 1-sulfate and 4-sulfate, as pale brown powder.

IR spectrum $\nu_{max}^{KBr}$ cm$^{-1}$: 1560 (COOK), 1260 (S=O), 1050 (C—O—S)

NMR (D$_2$O) δ: 1.70 (3H, s, =CCH$_3$), 1.95 & 2.04 (3H, s, CH$_3$ on the ring), 2.19 (4H, b, CH$_2$COO, =CCH$_2$), 3.27 (2H, m, CH$_2$ on the ring), 3.67 (3H, s, OCH$_3$), 3.77 (3H, s, OCH$_3$)

UV spectrum $\lambda_{max}^{H2O}$ nm: 273, 280

EXAMPLE 6

Sodium salt (200 mg) of 2,3-dimethoxy-6-(3-methoxycarbonylpropyl)-5-methylhydroquinone 4-sulfate prepared in Example 2 was dissolved in 1N NaOH (1.0 ml). The solution was heated at 60° C. for 30 minutes, and then made to pH 8 with diluted hydrochloric acid, followed by evaporation to dryness under reduced pressure. To the residue was added ethanol. The resulting insolubles were removed by filtration under heating. The filtrate was subjected to evaporation to dryness under reduced pressure. The resulting powder was washed with chloroform to give disodium salt (170 mg) of 6-(3-carboxypropyl)-2,3-dimethoxy-5-methylhydroquinone 4-sulfate.

IR spectrum $\nu_{max}^{KBr}$ cm$^{-1}$: 1570 (COONa), 1260 (S=O), 1050 (C—O—S)

NMR (D$_2$O) δ: 1.73 (2H, q, J=7.6 Hz, CH$_2$), 2.25 (3H, s, CH$_3$ on the ring), 2.26 (2H, t, J=7.6 Hz, CH$_2$COO), 2.64 (2H, t, J=7.6 Hz, CH$_2$ on the ring), 3.86 (3H, s, OCH$_3$), 3.92 (3H, s, OCH$_3$)

UV specturm $\lambda_{max}^{H2O}$ nm: 275, 280.5

EXAMPLE 7

With methanol and p-toluene sulfonic acid, 6-(3-carboxypropyl)-2,3-dimethoxy-5-methyl-1,4-benzoquinone was converted into the corresponding methyl ester, which was converted to 2,3-dimethoxy-6-(3-methoxycarbonylpropyl)-5-methylhydroquinone by a conventional method. To this compound (2.0 g) dissolved in pyridine (10 ml) was added chlorosulfonic acid (1.225 g) under ice-cooling. The mixture was stirred at room temperature for 30 hours. The pH of the reaction mixture was made to 8 with 1N potassium carbonate, then unreacted substances were removed by extraction with ethylether. The aqueous layer was evaporated to dryness under reduced pressure. The residue was dissolved in 1N potassium hydroxide (5 ml), and the solution was heated at 60° C. for two hours. The reaction solution was subjected to evaporation to dryness under reduced pressure. The residue was put in methanol for dissolution, and insoluble portions were removed. The methanol solution was subjected to distillation under reduced pressure, and the residue was purified by means of a Sephadex G-15 column-chromalography. The resultant colorless oily substance was treated with methanol-ethylether to give, as white powder, a mixture (766 mg) of respective dipotassium salts of 6-(3-carboxypropyl)-2,3-dimethoxy-5-methylhydroquinone-1- and 4-sulfates.

IR spectrum $\nu_{max}^{KBr}$ cm$^{-1}$: 1560 (COOK), 1250 (S=O), 1040 (C—O—S)

NMR (D$_2$O) δ: 1.69 (2H, q, CH$_2$), 2.17 & 2.24 (3H, s, CH$_3$ on the ring), 2.26 (2H, t, CH$_2$COO), 2.64 & 2.72 (2H, t, CH$_2$ on the ring), 3.86 (3H, s, OCH$_3$), 3.92 (3H, s, OCH$_3$)

EXAMPLE 8

In a manner similar to Example 7, 6-(9-carboxynonyl)-2,3-dimethoxy-5-methyl-1,4-benzoquinone was esterified, which was then reduced to give 2,3-dimethoxy-6-(9-methoxycarbonyl nonyl)-5-methylhydroquinone. To this product (1.00 g) dissolved in pyridine (5 ml) was added chlorosulfonic acid (0.72 g) under ice-cooling. The mixture was stirred for three hours. To the reaction solution was added 1N potassium hydroxide to made the pH to 9–10. Unreacted substances were extracted with hexane. The aqueous layer was evaporated to dryness at 70° C. under reduced pressure. The residue was purified by means of a silica-gel column chromatography. From the fraction eluted with methanol-chloroform (1:4) was obtained a mixture (473 mg) of the respective potassium salts of 6-(9-carboxynonyl)-2,3-dimethoxy-5-methylhydroquinone 1- and 4-sulfates as colorless powder.

IR spectrum $\nu_{max}^{KBr}$ cm$^{-1}$: 1720 (COOH), 1250 (S=O), 1050 (C—O—S)

NMR (D$_2$O) δ: 1.21 (14H, b, CH$_2$), 2.10 & 2.21 (3H, s, CH$_3$ on the ring), 2.26 (2H, t, CH$_2$COO), 2.54 and 2.72 (2H, m, CH$_2$ on the ring), 3.83 (3H, s, OCH$_3$), 3.91 (3H, s, OCH$_3$)

From the second fraction was obtained dipotassium salt of 6-(9-carboxynonyl)-2,3-dimethoxy-5-methylhydroquinone 1,4-di-sulfate as colorless powder.

IR spectrum $\nu_{max}^{KBr}$ cm$^{-1}$: 1720 (COOH), 1250 (S=O), 1050 (C—O—S)

NMR (D$_2$O) δ: 1.29 (14H, b, CH$_2$), 2.29 (3H, s, CH$_3$ on the ring), 2.34 (2H, t, CH$_2$COO), 2.78 (2H, t, CH$_2$ on the ring), 3.94 (6H, s, OCH$_3$)

EXAMPLE 9

The mixture (100 mg) of the respective sodium salts of 6-(10-acetoxydecyl)-2,3-dimethoxy-5-methylhydroquinone 1- and 4-sulfate, which was obtained in Example 3, was subjected to a reaction similar to that in Example 6 to give a mixture (60 mg) of the respective sodium salts of 6-(10-hydroxydecyl)-2,3-dimethoxy-5-methylhydroquinone 1- and 4-sulfate as colorless powder.

IR spectrum $\nu_{max}^{KBr}$ cm$^{-1}$: 1260 (S=O), 1050 (C—O—S)

NMR (D$_2$O) δ: 1.21 (16H, b, CH$_2$), 2.10 & 2.21 (3H, s, CH$_3$ on the ring), 2.53 (2H, m, CH$_2$ on the ring), 3.53 (2H, t, J=6 Hz, CH$_2$O), 3.80 (3H, s, OCH$_3$), 3.89 (3H, s, OCH$_3$)

EXAMPLE 10

A mixture (1 g) of the respective potassium salts of 6-(10-acetoxydecyl)-2,3-dimethoxy-5-methylhydroquinone 1- and 4 sulfate, which was obtained in Example 4, was subjected to a reaction similar to that in Example 5. The resultant colorless powder was recrystallized from water to give potassium salt of 6-(10-hydroxydecyl)-2,3-dimethoxy-5-methylhydroquinone 4-sulfate as colorless needles, m.p. 178°–181° C.

NMR (D$_2$O) δ: 1.21 (16H, b, CH$_2$), 2.22 (3H, s, CH$_3$ on the ring), 2.54 (2H, m, CH$_2$ on the ring), 3.52 (2H, t, J=6 Hz, CH$_2$O), 3.81 (3H, s, OCH$_3$), 3.89 (3H, s, OCH$_3$)

Elemental Analysis for C$_{19}$H$_{31}$KO$_8$S: Calcd.: C,49.76; H,6.81; S,6.99; Found: C,49.74; H,6.72; S,6.93

U V spectrum: $\lambda_{max}^{H_2O}$ nm(ε): 273.5 (1090), 280 (1100)

From the mother liquor was obtained a mixture of potassium salts of 6-(10-hydroxydecyl)-2,3-dimethoxy-5-methylhydroquinone 1- and 4-sulfate as colorless powder.

IR spectrum $\nu_{max}^{KBr}$ cm$^{-1}$: 1280, 1230 (S=O), 1050 (C—O—S)

NMR (D$_2$O) δ: 1.20 (16H, b, CH$_2$), 2.10 & 2.22 (3H, s, CH$_3$ on the ring), 2.53 & 2.73 (2H, m, CH$_2$ on the ring), 3.51 (2H, t, J=6 Hz, CH$_2$O), 3.81 (3H, s, OCH$_3$), 3.90 (3H, s, OCH$_3$)

EXAMPLE 11

By a conventional method, 6-(11-acetoxyundecyl)-2,3-dimethoxy-5-methyl-1,4-benzoquinone (348 mg) was converted to 6-(11-acetoxyundecyl)-2,3-dimethoxy-5-methylhydroquinone, which was dissolved in pyridine (2 ml). The pyridine solution was worked up in a similar manner to that in Example 7 to give a mixture (118 mg) of potassium salts of 6-(11-hydroxyundecyl)-2,3-dimethoxy-5-methylhydroquinone 1- and 4-sulfate as white powder.

IR spectrum $\nu_{max}^{KBr}$ cm$^{-1}$ 1240, 1050 (SO$_2$)

NMR spectrum [in D$_2$O-CD$_3$OH (1:1)]δ: 1.28 (18H, b, CH$_2$), 2.11 & 2.22 (3H, s, CH$_3$ on the ring), 2.61 (2H, m, CH$_2$ on the ring), 3,53 (2H, t, CH$_2$O), 3.81 (3H, s, OCH$_3$), 3.90 (3H, s, OCH$_3$)

EXAMPLE 12

To a 10% KOH aqueous solution (30 ml) of 4-(2-hydroxy-3,4-dimethoxy-6-methylphenyl)butyric acid (2.5 g) was added dropwise under ice-cooling an aqueous solution (50 ml) of potassium persulfate (2.7 g) in the course of 4 hours. The mixture was left standing in a refrigerator overnight. To the reaction mixture was added dilute hydrochloric acid to make the pH 5, then unreacted materials (0.915 g) were recovered by extraction with ethyl acetate. The aqueous layer was made to pH 8 with a 10% aqueous solution of KOH, and then evaporated to dryness under reduced pressure. The residue was dissolved in methanol. Insoluble inorganic salts were removed by filtration. The methanol solution was batchwise subjected to filtration using silica-gel, and the filtrate was subjected three times to treatment with activated charcoal. The methanolic solution was evaporated to dryness under reduced pressure, and the residue was purified by means of a column-chromatography using Sephadex G-15 (1.2×68 cm). The fractions are evaporated to dryness under reduced pressure. The residue was treated with methanol-ethylether to give dipotassium salt of 6-(3-carboxypropyl)-2,3-dimethoxy-5-methylhydroquinone 4-sulfate as colorless powder. The yield was 0.678 g.

IR spectrum $\nu_{max}^{KBr}$ cm$^{-1}$: 1560 (COOK), 1250 (S=O), 1040 C—O—S)

NMR (D$_2$O) δ: 1.70 (2H, q, J=7.5 Hz, CH$_2$), 2.24 (3H, s, CH$_3$ on the ring), 2.26 (2H, t, CH$_2$COO), 2.65 (2H, t, J=7.5 Hz, CH$_2$ on the ring), 3.86 (3H, s, OCH$_3$), 3.92 (3H, s, OCH$_3$)

EXAMPLE 13

In a similar manner to Example 12, 10-(2-hydroxy-3,4-dimethoxy-6-methylphenyl)decanoic acid (5.74 g) was treated to obtain dipotassium salt of 6-(9-carboxynonyl)-2,3-dimethoxy-5-methylhydroquinone 4-sulfate as colorless powder.

IR spectrum $\nu_{max}^{KBr}$ cm$^{-1}$: 1570 (COOK), 1250 (S=O), 1050 (C—O—S)

NMR (D$_2$O) δ: 1.29 (14H, b, CH$_2$), 2.19 (2H, t, CH$_2$COO), 2.23 (3H, s, CH$_3$ on the ring), 2.56 (2H, t, CH$_2$ on the ring), 3.85 (3H, s, OCH$_3$), 3.93 (3H, s, OCH$_3$)

I claim:

1. A compound of the formula:

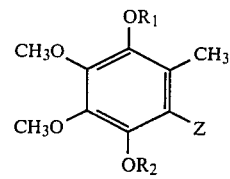

wherein either one of R$_1$ and R$_2$ is hydrogen or SO$_3$H and the other is SO$_3$H, Z is

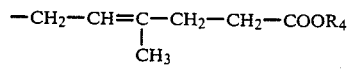

$$-CH_2-CH=C-CH_2-CH_2-COOR_4$$
$$\phantom{-CH_2-CH=}\overset{|}{CH_3}$$

where m is an integer of 1-22, n is an integer of 0-21, R$_3$ is hydrogen or alkanoyl having 2 to 4 carbon atoms, and R$_4$ is hydrogen or alkyl having 1 to 4 carbon atoms, or a pharmaceutically acceptable salt thereof.

2. A compound as claimed in claim 1, wherein R$_1$ stands for SO$_3$H and R$_2$ stands for hydrogen.

3. A compound as claimed in claim 1, wherein Z stands for $-(CH_2)_m-OR_3$.

4. A compound as claimed in claim 1, wherein Z stands for $-(CH_2)_n-COOR_4$.

5. A compound as claimed in claim 1, wherein the compound is in the form of a pharmacologically acceptable salt.

6. A compound as claimed in claim 1, wherein the compound is a potassium salt of 6-(10-hydroxydecyl)-2,3-dimethoxy-5-methylhydroquinone 4-sulfate.

7. A compound as claimed in claim 1, wherein the compound is a sodium salt of 6-(10-hydroxydecyl)-2,3-dimethoxy-5-methylhydroquinone 4-sulfate.

8. A compound as claimed in claim 1, wherein the compound is a dipotassium salt of 6-(9-carboxynonyl)-2,3-dimethoxy-5-methylhydroquinone 4-sulfate.

* * * * *